United States Patent
Schytte

(10) Patent No.: US 7,731,700 B1
(45) Date of Patent: Jun. 8, 2010

(54) SUBDERMAL INJECTION PORT

(76) Inventor: Walter Samuel Schytte, 2909 Trentwood Blvd., Orlando, FL (US) 32812

( * ) Notice: Subject to any disclaimer, the term of this patent is extended or adjusted under 35 U.S.C. 154(b) by 177 days.

(21) Appl. No.: 11/771,303

(22) Filed: Jun. 29, 2007

(51) Int. Cl.
A61M 37/00 (2006.01)
(52) U.S. Cl. .............................. 604/288.03; 604/288.01
(58) Field of Classification Search ................ 128/899; 604/244, 264, 288.03
See application file for complete search history.

(56) References Cited

U.S. PATENT DOCUMENTS

| 4,190,040 A | * | 2/1980 | Schulte ........................ 128/899 |
| 4,217,889 A | | 8/1980 | Radovan et al. |
| 4,433,440 A | | 2/1984 | Cohen |
| 4,543,088 A | | 9/1985 | Bootman et al. |
| 4,615,704 A | | 10/1986 | Frisch |
| 4,643,733 A | | 2/1987 | Becker |
| 4,651,717 A | | 3/1987 | Jakubczak |
| 4,671,255 A | | 6/1987 | Dubrul et al. |
| 4,685,447 A | | 8/1987 | Iverson et al. |
| 4,738,657 A | | 4/1988 | Hancock et al. |
| 4,751,926 A | | 6/1988 | Sasaki |
| 4,773,908 A | | 9/1988 | Becker |
| 4,798,584 A | | 1/1989 | Hancock et al. |
| 4,817,637 A | | 4/1989 | Hillegass et al. |
| 4,832,054 A | * | 5/1989 | Bark ........................... 128/899 |
| 4,840,190 A | | 6/1989 | Sasaki |
| 4,840,615 A | | 6/1989 | Hancock et al. |
| 4,841,948 A | | 6/1989 | Bauer et al. |
| 4,908,029 A | | 3/1990 | Bark et al. |
| 4,944,749 A | | 7/1990 | Becker |
| 4,950,292 A | | 8/1990 | Audretsch |
| 4,969,899 A | | 11/1990 | Cox |
| 5,066,303 A | | 11/1991 | Bark et al. |
| 5,074,878 A | | 12/1991 | Bark et al. |
| 5,133,753 A | | 7/1992 | Bark et al. |
| 5,146,933 A | | 9/1992 | Boyd |
| 5,167,638 A | * | 12/1992 | Felix et al. ................... 604/175 |
| 5,201,715 A | | 4/1993 | Masters |
| 5,423,334 A | | 6/1995 | Jordan |
| 5,425,760 A | | 6/1995 | Rosenberg |
| 5,480,430 A | | 1/1996 | Carlisle et al. |
| 5,578,085 A | | 11/1996 | Johnson, Jr. et al. |
| 6,190,352 B1 | * | 2/2001 | Haarala et al. ............ 604/93.01 |
| 6,582,465 B2 | | 6/2003 | Tse |
| 6,743,254 B2 | | 6/2004 | Guest et al. |
| 2001/0004709 A1 | | 6/2001 | Dubrul |
| 2002/0002402 A1 | | 1/2002 | Tse |
| 2002/0143300 A1 | * | 10/2002 | Trombley et al. ............ 604/247 |
| 2003/0149481 A1 | | 8/2003 | Guest et al. |
| 2006/0069403 A1 | | 3/2006 | Shalon et al. |

* cited by examiner

Primary Examiner—Nicholas D Lucchesi
Assistant Examiner—Gerald Landry, II
(74) Attorney, Agent, or Firm—Douglas J Visnius

(57) ABSTRACT

A subdermal injection port may include a housing, a first chamber within the housing, and a second chamber within the housing. The subdermal injection port may also include a needle stop between the first chamber and the second chamber. The subdermal injection port may further include an outlet in the housing, with the outlet being in fluid communication with the first chamber and the second chamber.

5 Claims, 3 Drawing Sheets

SUBDERMAL INJECTION PORT

FIELD OF THE INVENTION

The invention relates to the field of injection ports, and, more particularly, to subdermal injection ports.

BACKGROUND OF THE INVENTION

Subdermal injection ports have been used in conjunction with tissue expanders. For instance, U.S. Pat. No. 4,217,889 to Radovan et al., U.S. Pat. No. 4,615,704 to Frisch, U.S. Pat. No. 4,651,717 to Jakubczak, and U.S. Pat. No. 5,423,334 to Jordan may disclose single-sided subdermal injection ports in fluid communication with an inflatable tissue expander.

Other references have alternate configurations such as U.S. Pat. No. 5,074,878 to Bark et al. which may disclose a subdermal tissue expander having a shell defining a chamber. In this reference, a self-sealing layer may line the chamber and a needle stop may be positioned within the chamber.

Another configuration is disclosed by U.S. Pat. No. 4,817,637 to Hillegass et al. which may teach a subdermal injection port having a round smooth needle stop floating in a spherical housing. Yet another configuration is disclosed by U.S. Pat. No. 6,582,465 to Tse which may teach a single-sided injection port having multiple passageways for filling a tissue expander.

SUMMARY OF THE INVENTION

Advantages in accordance with the various embodiments of the invention are provided by a subdermal injection port that may include a housing, a first chamber within the housing, and a second chamber within the housing. The subdermal injection port may also include a needle stop between the first chamber and the second chamber. The subdermal injection port may further include an outlet in the housing, with the outlet being in fluid communication with the first chamber and the second chamber.

The first chamber and the second chamber may each include a self-sealing layer. The outlet may include a valve. The outlet may be in fluid communication with a swivel outside of the housing. The outlet's fluid communication with the first chamber may be independent of the second chamber, and the outlet's fluid communication with the second chamber may be independent of the first chamber.

The needle stop may be securely positioned between the first chamber and the second chamber. The needle stop may move relative to the first chamber and the second chamber. The needle stop may include a first side and a second side, and the first side and second side may each have a raised portion adjacent each side's periphery. The needle stop may include an opening permitting fluid communication between the first chamber and the second chamber. The needle stop may be substantially flat.

The housing adjacent the first chamber may include a substantially curved section opposite the needle stop. The housing adjacent the second chamber may include a substantially flat section opposite the needle stop.

Another embodiment of the subdermal injection port may include a housing, a first chamber within the housing, and a second chamber within the housing. The subdermal injection port may also include a needle stop between the first chamber and the second chamber, and the needle stop may include a first side and a second side. The subdermal injection port may further include a raised portion adjacent each of the first and second side's periphery. Additionally, the subdermal injection port may include an outlet in the housing, and the outlet may be in fluid communication with the first chamber and the second chamber. Further, the subdermal injection port may include a substantially flat section of the housing adjacent the second chamber and opposite the needle stop.

Other embodiments of the subdermal injection port may include a housing, a first chamber within the housing, and a second chamber within the housing. The subdermal injection port may also include a needle stop between the first chamber and the second chamber, and an outlet in the housing. The outlet may be in fluid communication with the first chamber and the second chamber. The subdermal injection port may further include a swivel outside of the housing in fluid communication with the outlet. Additionally, the subdermal injection port may include a substantially flat section of the housing adjacent the second chamber and opposite the needle stop.

BRIEF DESCRIPTION OF THE DRAWINGS

FIG. 5 is a side-perspective view of the swivel in FIG. 2.

DETAILED DESCRIPTION OF THE PREFERRED EMBODIMENTS

The invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Figure 1:
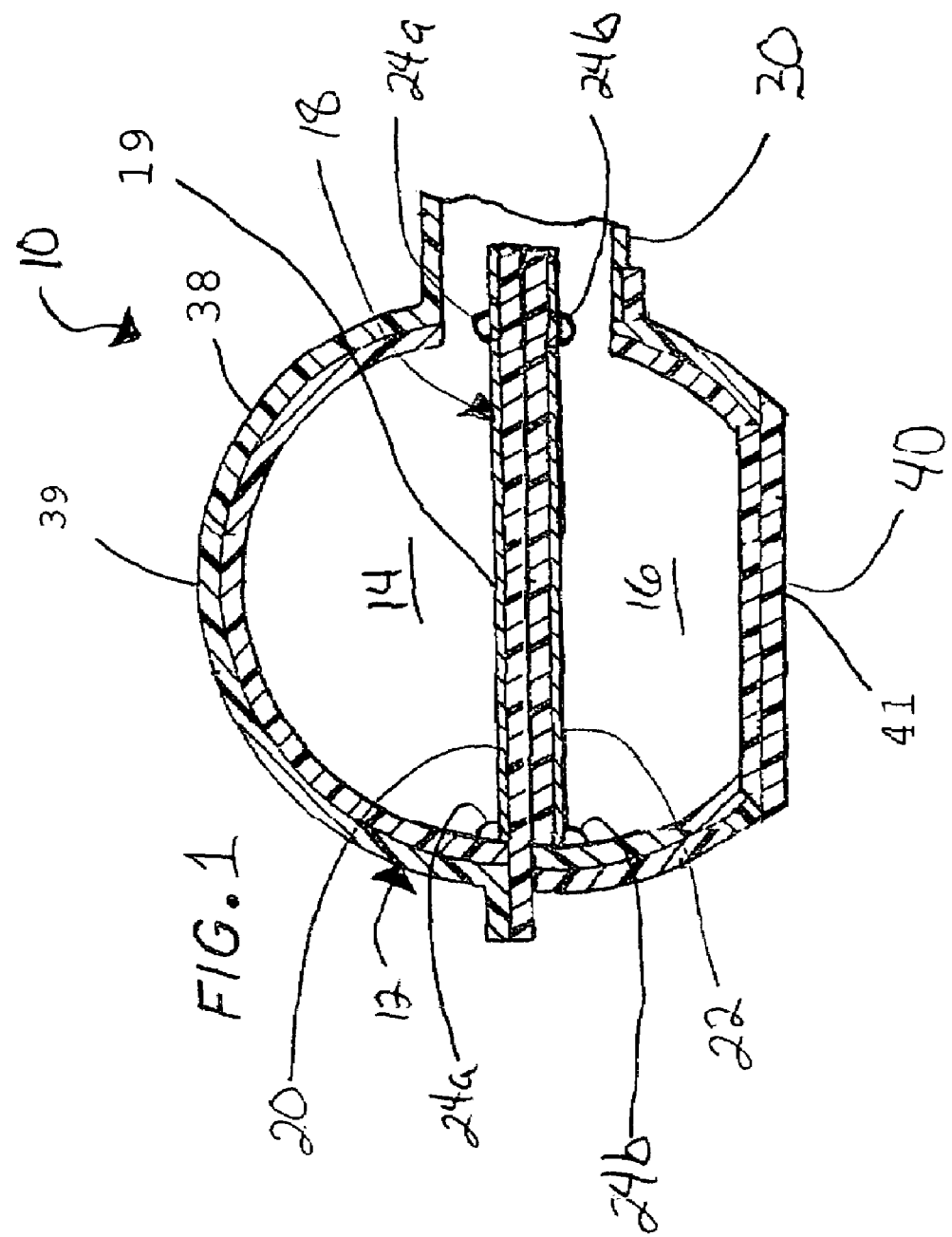
FIG. 1 is a cross-sectional view of a subdermal injection port in accordance with the invention.
Figure 2:
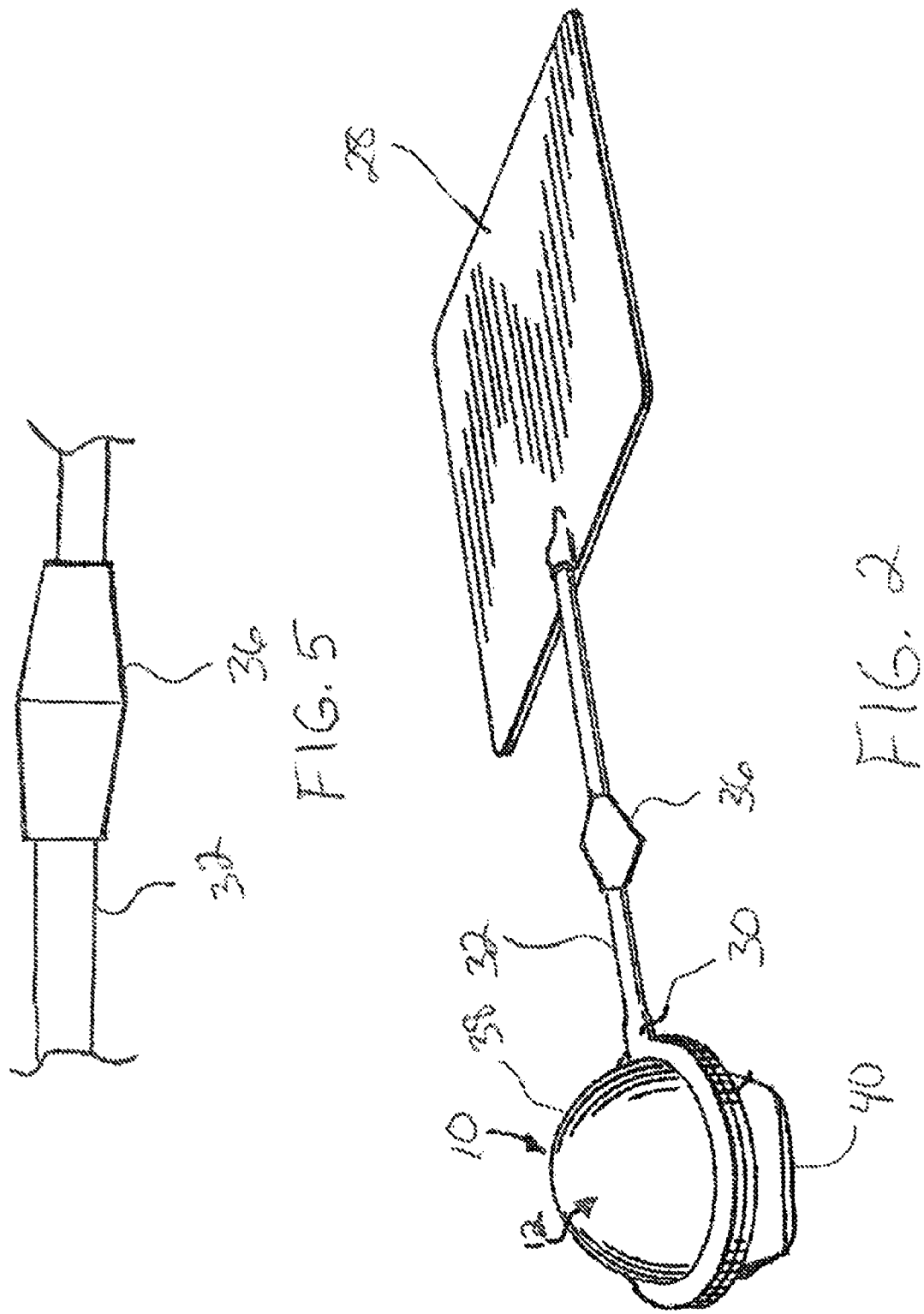
FIG. 2 is a side-perspective view of a tissue expander combined with the subdermal injection port of FIG. 1.

Referring initially to FIGS. 1 and 2, one embodiment of a subdermal injection port 10 is initially described. The subdermal injection port 10 includes a housing 12 made of biocompatible materials such as silicone, plastic, any combination of the foregoing, or the like. The choice of material may be determined based upon the time period in which the subdermal injection port 10 will reside inside a patient's body.

For example, if the subdermal injection port 10 is attached to a tissue expander 28, which is generally inserted into the body of a patient for a short period of time, then silicone may be the material of choice as will be appreciated by those of skill in the art. Alternatively, if the subdermal injection port 10 functions as a longer-term injection site, which may be used for administering pain medications, chemotherapy drugs, antibiotics, or the like, plastic may be the material of choice as will be appreciated by those of skill in the art.

The housing 12 includes a first chamber 14 and a second chamber 16 within the housing, for example. The first chamber 14 and the second chamber 16 include a self-sealing layer. In other words, if either the first chamber 14 or the second chamber 16 is penetrated by a needle, and then the needle is removed, the penetrated chamber will not readily transmit fluid from the needle entry site.

The housing 12 also includes a needle stop 18 between the first chamber 14 and the second chamber 16. The needle stop 18 is substantially flat although other geometries will work as well. The needle stop 18 comprises a first point centered 19 in the needle stop. The needle stop 18 includes a first side 20 and a second side 22, for example.

The first side 20 and second side 22 each has a respective raised portion 24a and 24b adjacent each side's periphery, for example. The raised portions 24a and 24b serve to limit the movement within its respective boundaries of a needle tip (not shown) when the needle tip is touching either the first side 20 or the second side 22.

In one embodiment, the needle stop 18 is securely positioned between the first chamber 14 and the second chamber 16. In a different embodiment, the needle stop 18 moves relative to the first chamber 14 and the second chamber 18.

Figure 3:
FIG. 3 is top-perspective view of one embodiment of a needle stop in accordance with the invention.

Referring now additionally to FIG. 3, the needle stop 18' includes an opening 26' permitting fluid communication between the first chamber 14 and the second chamber 16. Alternatively, the needle stop 18 may be made of a fluid-permeable barrier that still resists penetrations of a needle tip such as metallic mesh, or the like, as will be appreciated by those of skill in the art.

The subdermal injection port 10 further includes an outlet 30 in the housing 12, with the outlet being in fluid communication with the first chamber 14 and the second chamber 16. The outlet 30 is connected by a supply tube 32 to the tissue expander 28, for instance.

In one embodiment, the outlet 30 is in fluid communication with a swivel 36 as illustrated in FIGS. 2 and 5. The swivel 36 permits the housing 12 to move independently of the tissue expander 28 while permitting fluid communication between the housing and the tissue expander, for example. In one embodiment, the swivel 36 is located outside of the housing 12. In another embodiment, the swivel 36 is incorporated into the outlet 30. In yet other embodiments, other configurations for the placement of the swivel 36 are possible as will be appreciated by those of skill in the art.

Figure 4:
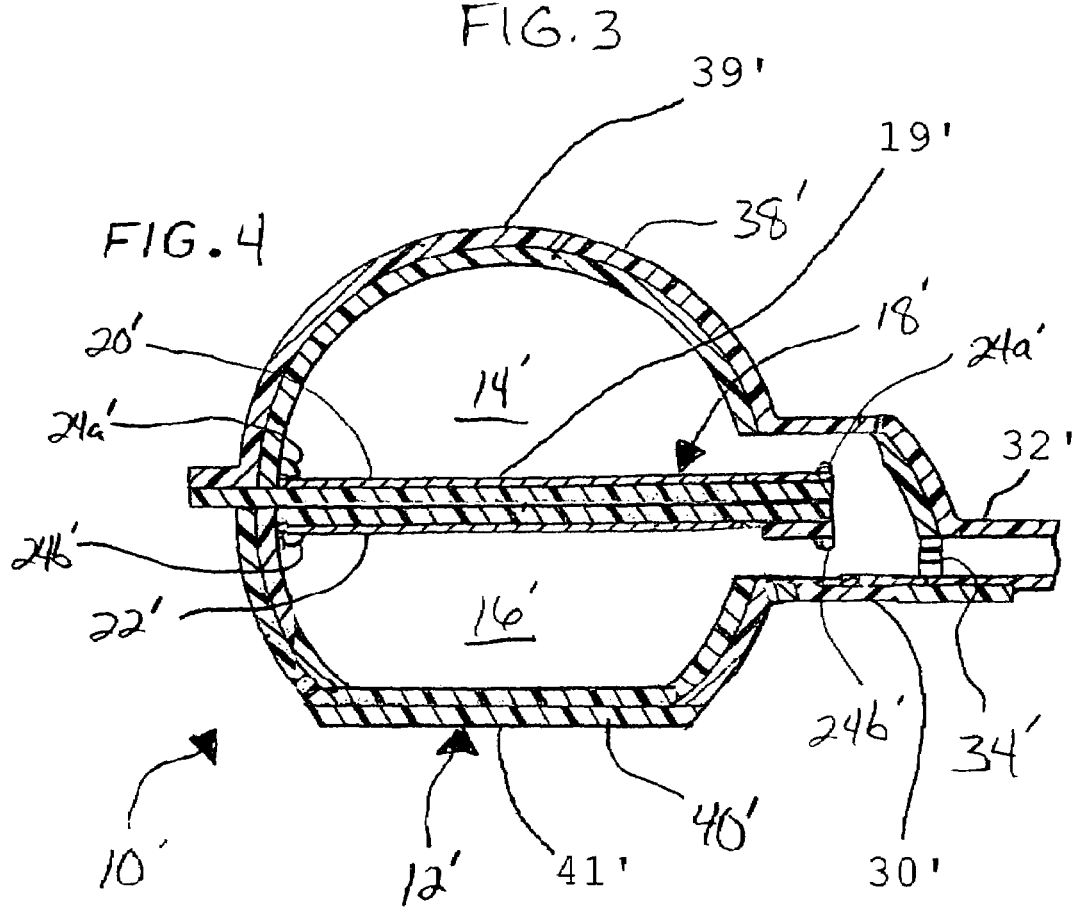
FIG. 4 is a cross-sectional view of another embodiment of the subdermal injection port in accordance with the invention.

Referring now additionally to FIG. 4, in one embodiment, the outlet 30' includes a valve 34'. The valve 34' may be a one-way valve, a two-way valve, or the like. The outlet's 30' fluid communication with the first chamber 14' may be independent of the second chamber 16' due to the positioning of the valve 34' or such. Alternatively, the outlet's 30' fluid communication with the second chamber 16' may be independent of the first chamber 14' due to the positioning of the valve 34' or such.

The housing 12 adjacent the first chamber 14 and opposite the needle stop 18 includes a substantially curved section 38. The substantially curved section 38 permits the tissue of a patient to readily slide across its surface. The substantially curved section 38 comprises a second point 39 centered in the substantially curved section.

The housing 12 adjacent the second chamber 16 and opposite the needle stop 18 includes a substantially flat section 40. The substantially flat section 40 comprises a third point 41 centered in the substantially flat section and substantially in-line with the first point 19 and the second point 39. The substantially flat section 40 helps to resist movement of the housing 12 within the patient's body thus helping to keep the substantially curved section 38 properly positioned. Stated another way, the substantially flat section 40 acts as a base to help keep the housing 12 oriented properly within a patient's body.

However, even with the substantially flat section 40, in certain limited circumstances, the housing 12 may flip. In this case, the second chamber 16 may be readily accessed by a needle thereby providing a fluid entry point similar to the first chamber 14. In addition, the swivel 36 will help to minimize the twisting in the supply tube 32 so that fluid communication between the housing 12 and the exit point of the supply tube is not reduced.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that other modifications and embodiments are intended to be included within the scope of the appended claims.

That which is claimed is:

1. A subdermal injection port comprising:
    a housing;
    a first chamber within said housing;
    a second chamber within said housing;
    a needle stop between said first chamber and said second chamber;
    a first point substantially centered in said needle stop;
    a substantially curved section of said housing adjacent said first chamber and opposite said needle stop;
    a second point substantially centered in said substantially curved section;
    an outlet in said housing, said outlet in fluid communication with said first chamber and said second chamber;
    a substantially flat section of said housing adjacent said second chamber and opposite said needle stop; and
    a third point substantially centered in said substantially flat section and substantially in-line with said first point and said second point, said first point substantially in-line with said second point and said third point, and said second point substantially in-line with said first point and said third point.

2. The subdermal injection port of claim 1 wherein said outlet is in fluid communication with a swivel.

3. The subdermal injection port of claim 1 wherein said outlet comprises a valve.

4. The subdermal injection port of claim 1 wherein said needle stop is securely positioned between said first chamber and said second chamber.

5. The subdermal injection port of claim 3 wherein said valve comprises a one-way valve.

* * * * *